United States Patent [19]
Yoon

[11] Patent Number: 5,984,939
[45] Date of Patent: Nov. 16, 1999

[54] MULTIFUNCTIONAL GRASPING INSTRUMENT WITH CUTTING MEMBER AND OPERATING CHANNEL FOR USE IN ENDOSCOPIC AND NON-ENDOSCOPIC PROCEDURES

[76] Inventor: InBae Yoon, 2101 Highland Ridge Dr., Phoenix, Md. 21131

[21] Appl. No.: 08/847,255

[22] Filed: May 1, 1997

Related U.S. Application Data

[63] Continuation-in-part of application No. 08/612,634, Mar. 6, 1996, and application No. 08/376,186, Jan. 20, 1995, Pat. No. 5,665,100, said application No. 08/612,634, is a continuation of application No. 08/281,814, Jul. 28, 1994, abandoned, said application No. 08/376,186, is a continuation-in-part of application No. 08/281,814, which is a continuation of application No. 08/073,193, Jun. 8, 1993, Pat. No. 5,334,209, which is a continuation of application No. 07/720,381, Jun. 25, 1991, Pat. No. 5,217,473, which is a division of application No. 07/446,555, Dec. 5, 1989, Pat. No. 5,026,379.

[51] Int. Cl.⁶ .................................................... A61B 17/04
[52] U.S. Cl. .......................... 606/170; 606/205; 606/139; 606/144
[58] Field of Search .................................. 606/141, 139, 606/170, 205, 144

[56] References Cited

U.S. PATENT DOCUMENTS

| 2,002,594 | 5/1935 | Wappler et al. . |
| 2,004,559 | 6/1935 | Wappler et al. . |
| 2,011,169 | 8/1935 | Wappler . |
| 2,028,635 | 1/1936 | Wappler . |
| 2,031,682 | 2/1936 | Wappler et al. . |
| 2,032,860 | 3/1936 | Wappler et al. . |
| 2,068,721 | 1/1937 | Wappler et al. . |
| 2,316,297 | 4/1943 | Southerland et al. . |
| 2,518,994 | 8/1950 | Miller . |
| 2,691,370 | 10/1954 | Wallace . |
| 3,827,277 | 8/1974 | Weston . |
| 3,856,016 | 12/1974 | Davis . |
| 3,870,048 | 3/1975 | Yoon . |
| 3,871,379 | 3/1975 | Clarke . |
| 3,911,923 | 10/1975 | Yoon . |
| 3,958,576 | 5/1976 | Komiya . |
| 3,967,625 | 7/1976 | Yoon . |
| 3,980,086 | 9/1976 | Kletschka et al. . |
| 3,989,049 | 11/1976 | Yoon . |
| 4,049,002 | 9/1977 | Kletschka et al. . |
| 4,077,412 | 3/1978 | Moossun . |
| 4,085,743 | 4/1978 | Yoon . |
| 4,103,680 | 8/1978 | Yoon . |
| 4,174,715 | 11/1979 | Hasson . |
| 4,226,239 | 10/1980 | Polk et al. . |
| 4,249,533 | 2/1981 | Komiya . |
| 4,249,535 | 2/1981 | Komiya . |
| 4,257,420 | 3/1981 | Terayama . |
| 4,274,415 | 6/1981 | Kanamoto et al. . |
| 4,372,295 | 2/1983 | Heckele . |
| 4,374,523 | 2/1983 | Yoon . |
| 4,393,872 | 7/1983 | Reznik et al. . |

(List continued on next page.)

FOREIGN PATENT DOCUMENTS 2469912  11/1979  France .

Primary Examiner—Gary Jackson

[57] ABSTRACT

A multifunctional instrument for use in performing endoscopic and open surgical procedures within an anatomical cavity includes a handle and an elongate tubular member having a proximal end coupled with the handle for being disposed externally of the anatomical cavity and a distal end for being disposed within the anatomical cavity and carrying a pair of opposed, relatively movable jaws. The jaws are operable by manipulation of the handle to grasp objects, such as needles, and to cut objects, such as suture material and tissue. In addition, the elongate tubular member defines an operating channel permitting fluids and other instruments to be communicated at the operative site without the need of having to remove the instrument from the body.

28 Claims, 7 Drawing Sheets

U.S. PATENT DOCUMENTS

| | | |
|---|---|---|
| 4,427,014 | 1/1984 | Bel et al. . |
| 4,471,766 | 9/1984 | Terayama . |
| 4,484,581 | 11/1984 | Martin et al. . |
| 4,493,319 | 1/1985 | Polk et al. . |
| 4,557,255 | 12/1985 | Goodman . |
| 4,598,699 | 7/1986 | Garren et al. . |
| 4,644,951 | 2/1987 | Bays . |
| 4,662,371 | 5/1987 | Whipple et al. . |
| 4,669,470 | 6/1987 | Brandfield . |
| 4,674,501 | 6/1987 | Greenberg . |
| 4,712,545 | 12/1987 | Honkanen . |
| 4,739,760 | 4/1988 | Chin et al. . |
| 4,777,950 | 10/1988 | Kees, Jr. . |
| 4,788,966 | 12/1988 | Yoon . |
| 4,860,746 | 8/1989 | Yoon . |
| 4,869,268 | 9/1989 | Yoon . |
| 4,935,027 | 6/1990 | Yoon . |
| 4,949,717 | 8/1990 | Shaw . |
| 4,961,743 | 10/1990 | Kees, Jr. et al. . |
| 4,966,583 | 10/1990 | Debbas ................................. 604/98 |
| 4,985,030 | 1/1991 | Melzer et al. . |
| 4,990,152 | 2/1991 | Yoon . |
| 5,015,249 | 5/1991 | Nakao et al. . |
| 5,025,778 | 6/1991 | Silverstein et al. .................... 128/4 |
| 5,026,379 | 6/1991 | Yoon . |
| 5,037,433 | 8/1991 | Wilk et al. ......................... 606/139 |
| 5,049,153 | 9/1991 | Nakao et al. . |
| 5,099,827 | 3/1992 | Melzer et al. . |
| 5,100,418 | 3/1992 | Yoon et al. . |
| 5,139,487 | 8/1992 | Baber ................................. 604/165 |
| 5,147,356 | 9/1992 | Bhatta . |
| 5,147,357 | 9/1992 | Rose et al. . |
| 5,147,373 | 9/1992 | Ferzli ................................. 606/144 |
| 5,152,780 | 10/1992 | Honkanen et al. . |
| 5,156,608 | 10/1992 | Troidl et al. . |
| 5,156,609 | 10/1992 | Nakao et al. . |
| 5,170,800 | 12/1992 | Smith et al. . |
| 5,171,250 | 12/1992 | Yoon . |
| 5,171,258 | 12/1992 | Bales et al. . |
| 5,172,700 | 12/1992 | Bencini et al. . |
| 5,176,695 | 1/1993 | Dulebohn . |
| 5,176,700 | 1/1993 | Brown et al. . |
| 5,190,541 | 3/1993 | Abele et al. .......................... 606/46 |
| 5,192,298 | 3/1993 | Smith et al. . |
| 5,196,023 | 3/1993 | Martin . |
| 5,203,785 | 4/1993 | Slater . |
| 5,211,650 | 5/1993 | Noda ................................. 606/139 |
| 5,211,655 | 5/1993 | Hasson . |
| 5,217,030 | 6/1993 | Yoon . |
| 5,217,460 | 6/1993 | Knoepfler . |
| 5,217,473 | 6/1993 | Yoon . |
| 5,219,354 | 6/1993 | Choudhury et al. . |
| 5,220,928 | 6/1993 | Oddsen et al. . |
| 5,222,961 | 6/1993 | Nakao et al. . |
| 5,222,962 | 6/1993 | Burkhart . |
| 5,222,976 | 6/1993 | Yoon . |
| 5,226,908 | 7/1993 | Yoon . |
| 5,234,443 | 8/1993 | Phan et al. ......................... 606/148 |
| 5,261,917 | 11/1993 | Hasson et al. ...................... 606/139 |
| 5,300,087 | 4/1994 | Knoepfler . |
| 5,312,391 | 5/1994 | Wilk ................................. 606/1 |
| 5,318,589 | 6/1994 | Lichtman . |
| 5,324,254 | 6/1994 | Phillips ............................. 604/21 |
| 5,334,199 | 8/1994 | Yoon . |
| 5,334,209 | 8/1994 | Yoon . |
| 5,336,231 | 8/1994 | Adair ................................. 606/148 |
| 5,342,381 | 8/1994 | Tidemand . |
| 5,342,389 | 8/1994 | Haber et al. . |
| 5,342,390 | 8/1994 | Slater et al. . |
| 5,348,555 | 9/1994 | Zinnanti ............................. 606/49 |
| 5,366,459 | 11/1994 | Yoon . |
| 5,366,476 | 11/1994 | Noda ................................. 606/206 |
| 5,398,670 | 3/1995 | Ortiz et al. ........................ 128/6 |
| 5,403,332 | 4/1995 | Christoudias ...................... 606/148 |
| 5,462,561 | 10/1995 | Voda ................................. 606/144 |
| 5,462,562 | 10/1995 | Elkus ................................. 606/148 |
| 5,472,439 | 12/1995 | Hurd ................................. 606/1 |
| 5,476,505 | 12/1995 | Limon ................................. 623/1 |
| 5,496,310 | 3/1996 | Exconde et al. ..................... 606/205 |
| 5,538,008 | 7/1996 | Crowe ................................. 128/751 |
| 5,542,949 | 8/1996 | Yoon ................................. 606/143 |
| 5,549,623 | 8/1996 | Sharpe et al. ...................... 606/171 |
| 5,562,102 | 10/1996 | Taylor ................................. 128/751 |
| 5,569,241 | 10/1996 | Edwards ............................. 604/41 |
| 5,578,007 | 11/1996 | Imran ................................. 604/95 |
| 5,607,435 | 3/1997 | Sachdeva et al. ................... 606/139 |
| 5,611,813 | 3/1997 | Lichtman ........................... 606/205 |
| 5,620,415 | 4/1997 | Lucey et al. ....................... 604/22 |
| 5,620,459 | 4/1997 | Lichtman ........................... 606/205 |
| 5,669,927 | 9/1997 | Boebel et al. ...................... 606/180 |
| 5,690,606 | 11/1997 | Slotman ............................. 600/206 |

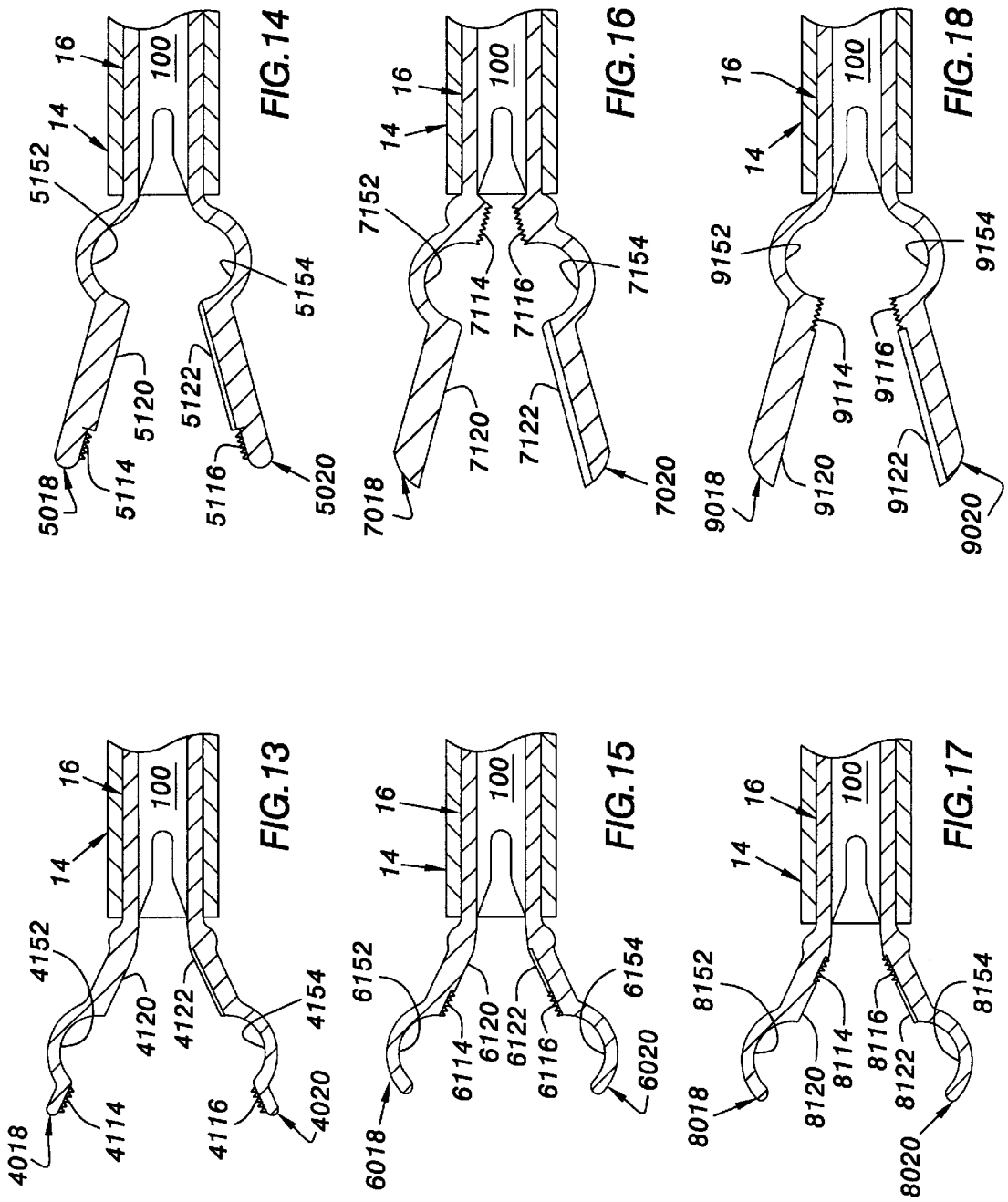

MULTIFUNCTIONAL GRASPING INSTRUMENT WITH CUTTING MEMBER AND OPERATING CHANNEL FOR USE IN ENDOSCOPIC AND NON-ENDOSCOPIC PROCEDURES

CROSS-REFERENCE TO RELATED APPLICATIONS

This application is a continuation-in-part of pending patent application Ser. No. 08/612,634, filed Mar. 6, 1996, and Ser. No. 08/376,186, filed Jan. 20, 1995, now U.S. Pat. No. 5,665,100, which are a continuation and a continuation-in-part, respectively, of patent application Ser. No. 08/281,814, filed Jul. 28, 1994, abandoned, which is a continuation of patent application Ser. No. 08/073,193, filed Jun. 8, 1993, now U.S. Pat. No. 5,334,209, which is a continuation of patent application Ser. No. 07/720,381, filed Jun. 25, 1991, now U.S. Pat. No. 5,217,473, which is a division of U.S. patent application Ser. No. 07/446,555, filed Dec. 5, 1989, now U.S. Pat. No. 5,026,379, the disclosures of which are incorporated herein by reference.

This application is also related to patent applications Ser. No. 08/760,245, filed on Dec. 4, 1996, Ser. No. 08/778,710, filed on Dec. 27, 1996, and Ser. Nos. 08/847,183, 08/847,184, 08/847,185, 08/847,187, 08/847,188 and 08/847,190, which were filed on May 1, 1997.

BACKGROUND OF THE INVENTION

1. Field of the Invention

The present invention relates generally to medical procedures and instruments and, more particularly, to an instrument for grasping and cutting objects during endoscopic and open surgery.

2. Discussion of the Related Art

Endoscopic and minimally invasive medical procedures, such as laparoscopy, have become widely accepted for surgery and diagnosis due to the associated advantages relating to reduced trauma and hospitalization time. The performance of an endoscopic procedure typically involves creation of one or more puncture sites through a wall of an anatomical cavity using a penetrating instrument including an obturator, such as a trocar, disposed within a portal sleeve. After the penetrating instrument has penetrated into the anatomical cavity, the obturator is withdrawn leaving the sleeve in place to form a portal in the cavity wall for the introduction of instruments such as endoscopes, ligating appliers, forceps, cauteries and the like into the anatomical cavity.

Endoscopic procedures commonly involve performing a number of individual acts or functions within the anatomical cavity including grasping, cutting, coagulating, irrigating, aspirating, puncturing, injecting, dissecting, cauterizing, ligating, suturing, illuminating, visualizing and/or collecting specimens for biopsy. However, most endoscopic instruments are designed to perform only one of the above functions, requiring several incisions for placement of multiple portal sleeves to accommodate a suitable number of endoscopic instruments for performing the required functions or necessitating frequent withdrawal and replacement of individual endoscopic instruments through a single incision. While it is generally desirable to minimize the number of incisions created for performing a particular endoscopic procedure, substitution of instruments through a single incision can be time consuming, depending on the efficiency of the medical facility and staff, increasing the period of anesthetization for the patient. Additionally, internal bleeding can develop during the substitution of instruments thereby obscuring the field of view and requiring time consuming clean-up procedures to be performed.

A disadvantage of endoscopic instruments having articulated jaws, in particular, is that the jaws are typically mounted on pivots at the distal end of relatively long shafts requiring complicated and space-consuming linkages for converting the user's proximal movements into motion of the jaws increasing the risk of fluid leaking through poorly sealed pivotal mounts.

SUMMARY OF THE INVENTION

Accordingly, it is a primary object of the present invention to overcome the above-mentioned disadvantages of the prior art with an instrument capable of performing multiple functions.

Another object of the present invention is to permit multiple functions to be performed with a single instrument while defining a channel through the instrument for introducing and/or removing other instruments, fluids and objects at the operative site so that other functions can be performed without the need of having to remove the instrument from the body.

Some of the advantages of the present invention over the prior art are that the instrument can perform multiple functions through a single incision thereby minimizing the number of incisions required to perform an endoscopic procedure, that the frequency of substitution of instruments through a single incision can be reduced, that visualization of tissue through an operating channel formed through the instrument permits grasping and cutting operations to be performed with greater precision, that conventional handle structures can be used to provide users with a familiar feel and to decrease adaptation time, that the instrument can be fabricated at low cost using simple mechanisms without complicated linkages, and that the instrument can be sterilized for reuse or disposable for single patient use as desired.

These and other objects, advantages and benefits are realized with the present invention as generally characterized in an instrument including a handle and an elongate member having a proximal end coupled with the handle for being disposed externally of the anatomical cavity and a distal end for being disposed within the anatomical cavity and carrying a pair of opposed, relatively movable jaws. The jaws are operable by manipulation of the handle to perform multiple functions such as, for example, grasping objects such as needles and cutting objects such as tissue. In addition, a channel is defined along the elongate member to provide access to the operative site from outside the anatomical cavity without the need of having to remove the instrument from the cavity.

Other objects and advantages of the present invention will become apparent from the following description of the preferred embodiments taken in conjunction with the accompanying drawings, wherein like parts in each of the several figures are identified by the same reference numerals or by reference numerals having the same last three digits.

BRIEF DESCRIPTION OF THE DRAWINGS

FIGS. 13–20 are fragmentary side views, partly in section, of further modifications of the instrument jaws according to the present invention.

DESCRIPTION OF THE PREFERRED EMBODIMENTS

The multifunctional instrument of the present invention can be utilized in any type of anatomical cavity; and, accordingly, while the instrument is described hereinafter for use with a portal sleeve in endoscopic procedures, such as laparoscopy, the instrument can be used in open surgery and with catheters and other small or large diameter tubular or hollow, cylindrical members providing access to small cavities, such as veins and arteries, as well as large cavities, such as the abdomen.

Figure 1:
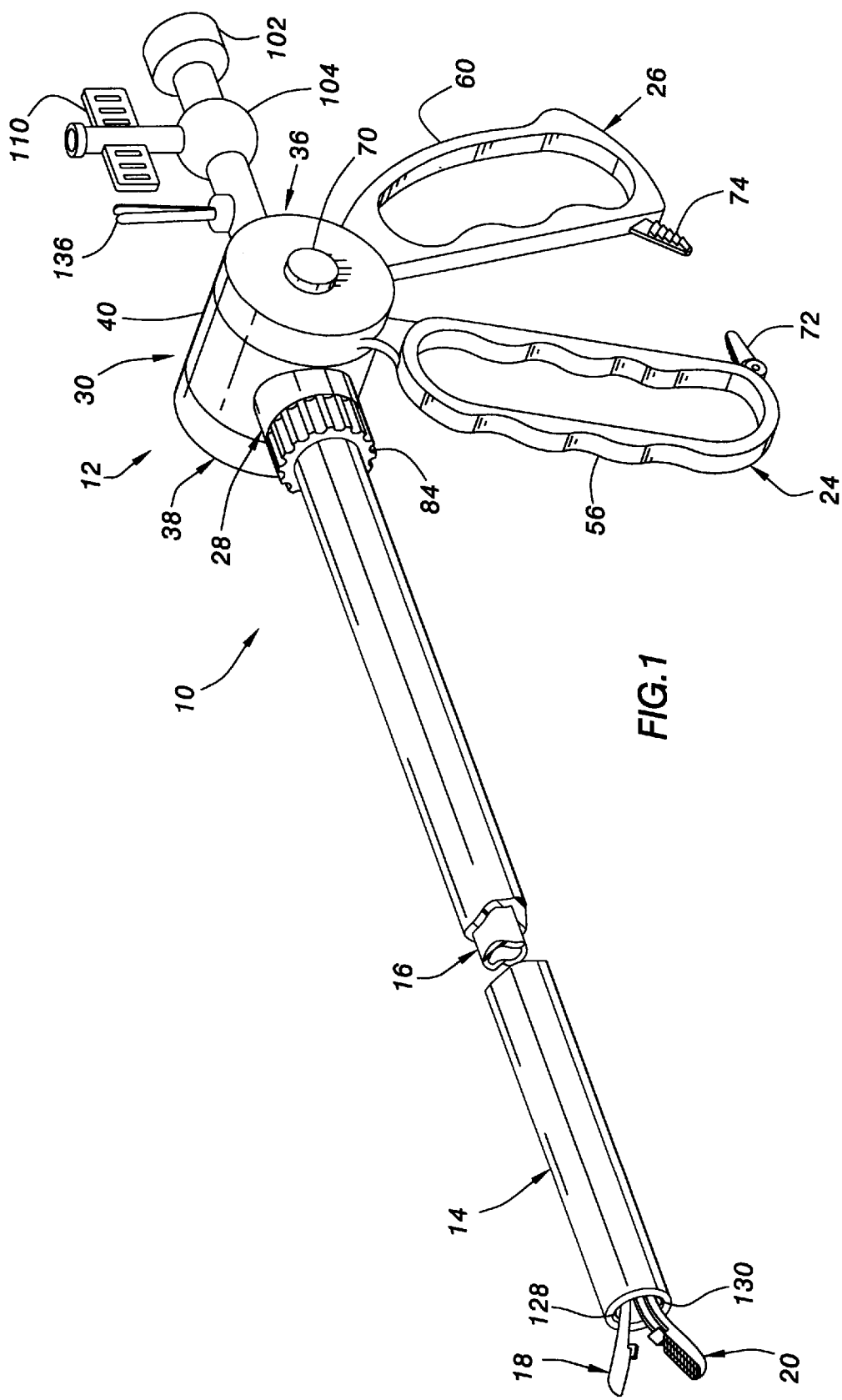
FIG. 1 is a perspective view, broken longitudinally, of a multifunctional instrument according to the present invention.
Figure 2:
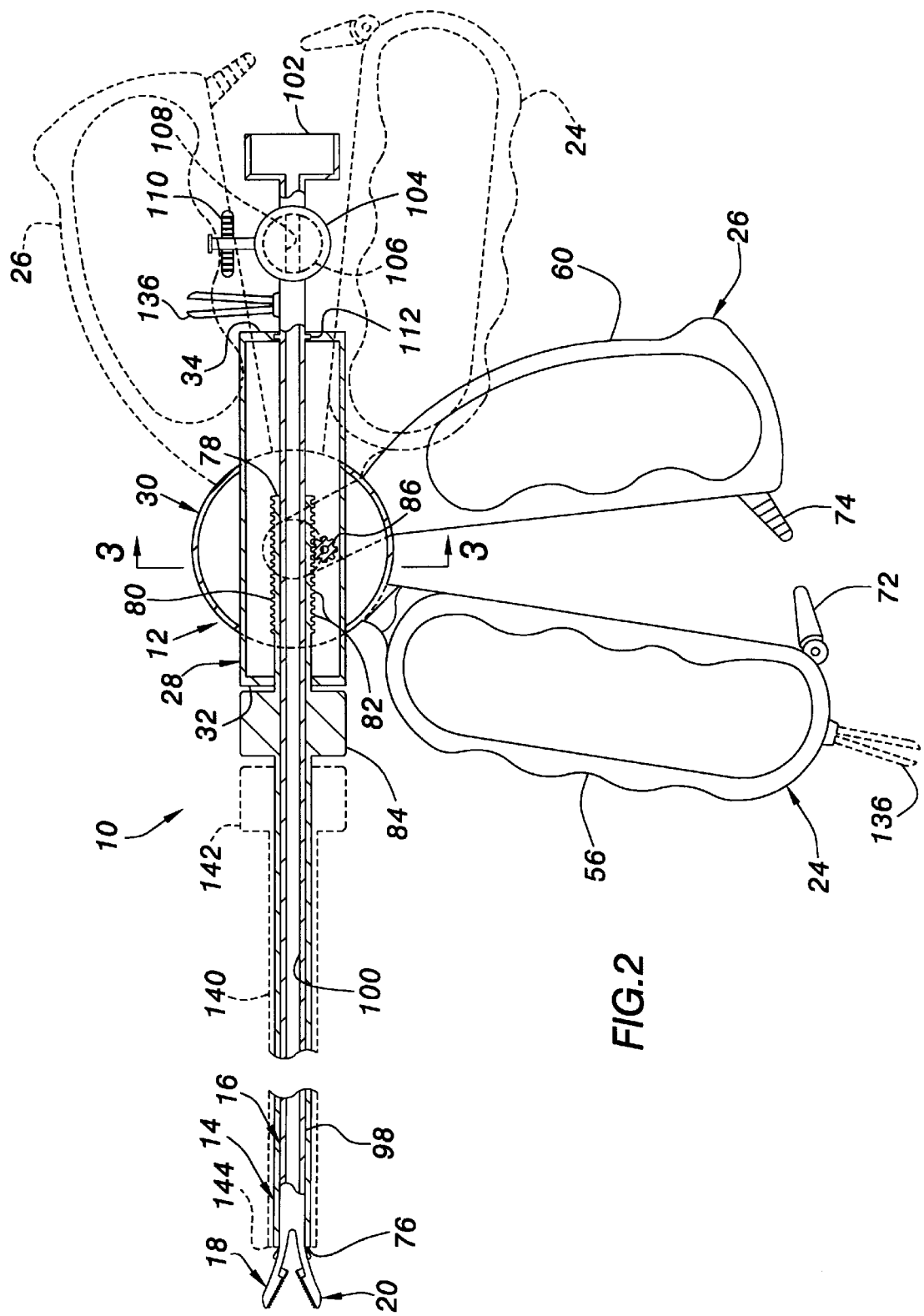
FIG. 2 is a broken side view, partly in section, of the multifunctional instrument of FIG. 1 with jaws of the instrument in an open position.

An instrument 10 in accordance with the present invention, as illustrated in FIGS. 1 and 2, includes a housing 12, an outer tubular member 14 extending distally from the housing, an inner tubular member 16 telescopically fitted within the outer tubular member and terminating distally in a pair of opposed jaws 18 and 20, and a handle portion formed of a fixed handle 24 and a movable handle 26.

Figure 3:
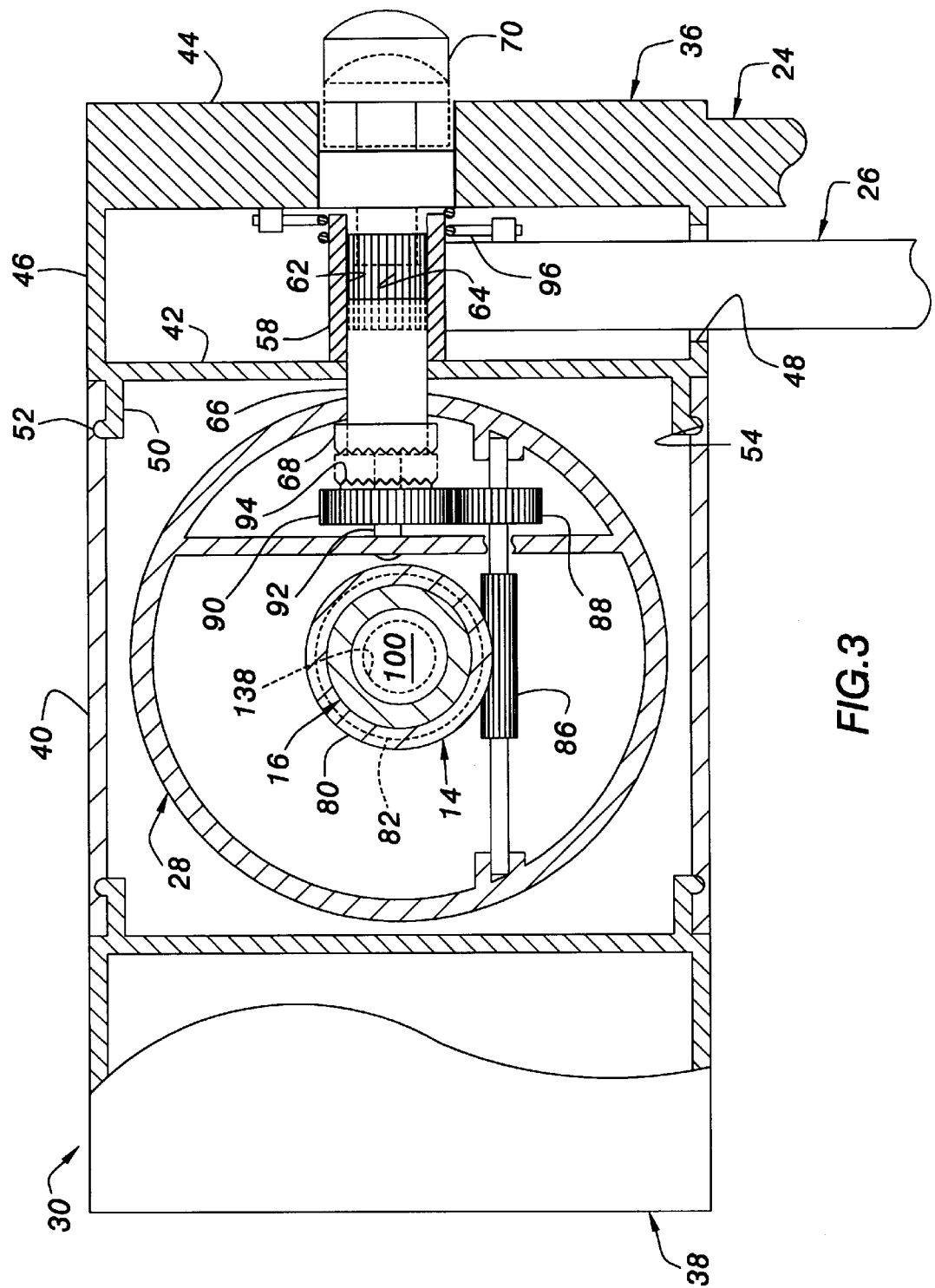
FIG. 3 is a cross-sectional view of the multifunctional instrument according to the present invention taken through line 3—3 in FIG. 2.

Housing 12 includes a first, longitudinal housing portion 28 of generally cylindrical configuration oriented coaxial with a central longitudinal axis of inner and outer tubular members 16 and 14, and a second, transverse housing portion 30 of generally cylindrical configuration oriented perpendicular to the first housing portion in a direction transverse to the longitudinal axis of the inner and outer tubular members. Longitudinal housing portion 28 extends through circular openings formed through longitudinally opposed sides of transverse housing portion 30 and includes front and rear walls 32 and 34 of generally circular configuration disposed on opposite sides of the transverse housing portion and oriented perpendicular to the longitudinal axes of the inner and outer tubular members. Transverse housing portion 30 includes a pair of laterally opposed end caps 36 and 38 of generally cylindrical configuration rotatably mounted on open ends of a centrally mounted cylindrical sleeve 40 through which the longitudinal housing portion extends. As best seen in FIG. 3, end cap 36 includes laterally spaced inner and outer walls 42 and 44 connected by a cylindrical side wall 46 with a slot 48 formed therein part way along the circumference of the wall. A cylindrical extension 50 of smaller diameter than cylindrical side wall 46 extends inwardly from inner wall 42 of the end cap to fit telescopically within cylindrical sleeve 40 when the inner wall abuts the open end of the sleeve. A flange or ring 52 extends outwardly from cylindrical extension 50 in a radial direction and is rotatably received within an annular recess or groove 54 formed along an inner surface of cylindrical sleeve 40 adjacent the open end of the sleeve.

Fixed handle 24 extends downwardly, looking at FIG. 2, from the cylindrical side wall of end cap 36 perpendicular to the longitudinal axis of the instrument or angled slightly towards the distal end of the instrument. A lower end of the fixed handle is configured as an elongate finger loop 56 to accommodate one or more fingers of the user. Movable handle 26 extends downwardly through slot 48, looking at FIG. 2, from a tubular end portion 58 disposed within end cap 36 to an elongate finger loop 60 configured to accommodate one or more fingers of the user and angularly spaced from finger loop 56 in a counterclockwise direction looking at FIG. 2. Tubular end portion 58 of movable handle 26 is disposed perpendicularly between inner and outer walls 42 and 44 of end cap 36 with a plurality of internal gear teeth 62 formed lengthwise therein to mesh with or engage external gear teeth 64 formed lengthwise along an outer surface of a shaft 66 extending inwardly from the outer wall of the end cap to a face gear 68 disposed within longitudinal housing portion 28 via an opening formed in a side wall of the longitudinal housing portion. A button 70 mounted in a recessed opening centrally formed through the outer wall 44 of the end cap is coupled with shaft 66 in a manner to produce, when depressed, inward movement of the shaft, as shown in FIG. 3, from a disengaged position shown by solid lines to an engaged position shown by broken lines. A pair of arcuate mating protrusions 72 and 74 are shown in FIGS. 1 and 2 as being mounted in opposed relation on finger loops 56 and 60 for ratcheting engagement during operational use to lock the handles in a number of angularly spaced positions relative to one another.

Outer tubular member 14 is open at both ends and extends distally from housing 12 through an opening in the front wall 32 of longitudinal housing portion 28. Distal end 76 of outer tubular member 14 can be blunt as shown, tapered, beveled, slotted or chamfered as desired or have any other suitable distal configuration. Preferably, outer tubular member 14 is made of a cylindrical length of a substantially rigid material, such as stainless steel or other medically acceptable metal or plastic materials. The proximal end 78 of the outer tubular member is movably disposed within longitudinal housing portion 28 and carries a rack 80 of generally cylindrical configuration with gear teeth 82 extending circumferentially around the proximal end of the outer tubular member in longitudinally spaced relation. A fluted collar 84 is disposed between proximal and distal ends of the outer tubular member adjacent the front wall of the housing and extends outwardly from the outer tubular member in a radial direction to provide a hand grip when rotating the handle about the longitudinal axis of the outer tubular member.

A pinion gear 86 engages the rack 80 and is mounted on the same shaft as a first transmission gear 88 which meshingly engages a second transmission gear 90 mounted on a shaft 92 telescopically received within button shaft 66 and having a face gear 94 mounted thereon in opposed relation to face gear 68 mounted on the inboard end of the button shaft. Looking at FIGS. 2 and 3, it will be appreciated that counterclockwise rotation of handle 26 about shaft 66 (in the sense of FIG. 2) results in proximal movement of outer tubular member 14 relative to housing 12 and that clockwise rotation of handle 26 about shaft 66 results in distal movement of outer tubular member 14 relative to housing 12. In a preferred embodiment, movable handle 26 is biased in a clockwise direction toward fixed handle 24, for example by use of a torsion spring 96 coiled around tubular end portion 58 and connected between the movable handle and the fixed handle and/or the housing.

Figure 4:
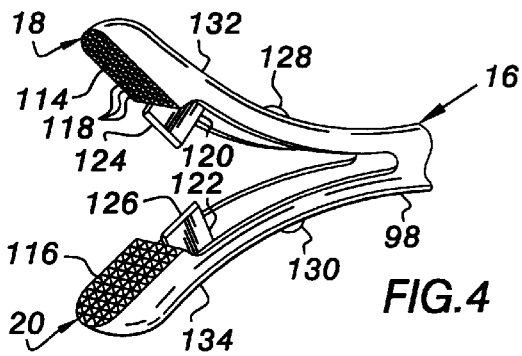
FIG. 4 is a fragmentary perspective view of the distal end of the multifunctional instrument of FIG. 1 with the jaws of the instrument in the open position.
Figure 6:
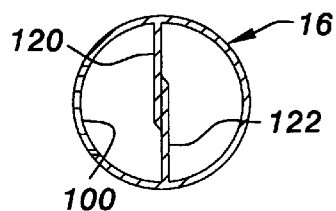
FIG. 6 is a cross-sectional view of the instrument jaws taken through line 6-6 in FIG. 5.

Inner member 16 includes an elongate tubular portion 98 telescopically fitted within outer tubular member 14 and defining a lumen or operating channel 100 of generally circular cross-section through the instrument. The proximal end of the inner member extends through the rear wall 34 of longitudinal housing portion 28 and terminates at a coupling 102, for example a Luer-type coupling or lock, for connection with sources of fluid or suction, other medical instruments and operating units such as those shown and described in my pending application Ser. No. 08/376,186, the disclosure of which has been incorporated herein by reference. A hollow, spherically-shaped valve housing 104 is distally spaced from the coupling within the housing, and a spherical valve member 106 having a cylindrical aperture or passage 108 formed therethrough is rotatably disposed within the valve housing and connected with a knob 110 extending upwardly through an opening in the spherical valve housing to permit manual operation of the valve. The inner member is fixed longitudinally relative to the housing with a flange 112 mounted between the coupling and the valve and received within a slotted recess formed in rear wall 34. The distal end of tubular portion 98 is bifurcated or split longitudinally to form integral one-piece jaws 18 and 20 in opposed relation, the jaws being normally biased apart in a lateral direction relative to the longitudinal axis of the inner member as shown in FIGS. 1, 2 and 4. Referring to FIG. 4, in particular, jaws 18 and 20 cooperate to define a grasping portion at a distal end having laterally opposed inner surfaces 114 and 116 formed with a conventional diamond-shaped tread made up of a repeating pattern of diamond-shaped protrusions or teeth 118 which extend inwardly, toward the central longitudinal axis of the inner member, to securely hold a suture needle, anatomical tissue or any other object when moved toward one another to a closed position. Jaws 18 and 20 also define a cutting portion proximally spaced from the grasping portion and including a pair of cutting members or blades 120 and 122 carried by the jaws in opposed relation. As best seen in FIG. 4, blades 120 and 122 are proximally spaced from grasping surfaces 114 and 116 and are mounted to project inwardly in alignment with the central longitudinal axis of each jaw in generally opposed relation so that sharp tissue cutting edges 124 and 126 of the blades slidingly engage one another like a scissors when the jaws are moved between the open position or condition shown in FIG. 2 and the closed position or condition shown in FIGS. 5 and 6. The blades are shown as being flat and straight with an orientation parallel to a longitudinal axis of the inner tubular member but can be oriented at any angle relative to the longitudinal axis of the inner tubular member, can be bent in or out of plane, or can be curved in or out of plane dependent upon procedural use. Wedge-like cams 128 and 130 protrude outwardly from respective laterally opposite outer surfaces 132 and 134 of jaws 18 and 20 and taper inwardly in the proximal direction to present an angled cam surface against which the distal end of outer tubular member 14 can act to force the jaws together.

Tubular body 98 of the inner member is preferably formed with jaws 18 and 20 as a single unitary part using a resilient medically-acceptable material such as, for example, a spring steel or a plastic material having suitable elastic properties for normally biasing the upper and lower jaws apart in a lateral direction transverse to a longitudinal axis of the inner member while permitting the jaws to be moved laterally toward one another in response to axial and/or laterally inward forces acting on the outer jaw surfaces and/or cams as a result of relative axial movement between the outer tubular member and the inner member. Blades 120 and 122 can be formed integrally with the jaws as a one-piece unit or formed separately of the jaws and connected thereto in any suitable manner such as, for example, by adhesive bonding, welding or mechanical attachment. Preferably, the blades are formed of a medical grade metal material such as stainless steel or titanium.

An insulated connector 136 can optionally be mounted on inner member 16 outside housing 12 or anywhere else on the instrument including, but not limited to, the fixed handle 24 as shown by broken lines in FIG. 2, to connect electrically conductive elements of the instrument with a source of electricity for performing unipolar or bipolar procedures such as electric coagulation, for example using one or both of the blades as conductive elements. In addition, an interior surface of operating channel 100 can be coated with an electrical and/or thermal insulating layer, shown by broken lines in FIG. 3 at 138, to permit safe insertion of electrical and/or thermal devices through the operating channel.

Figure 5:
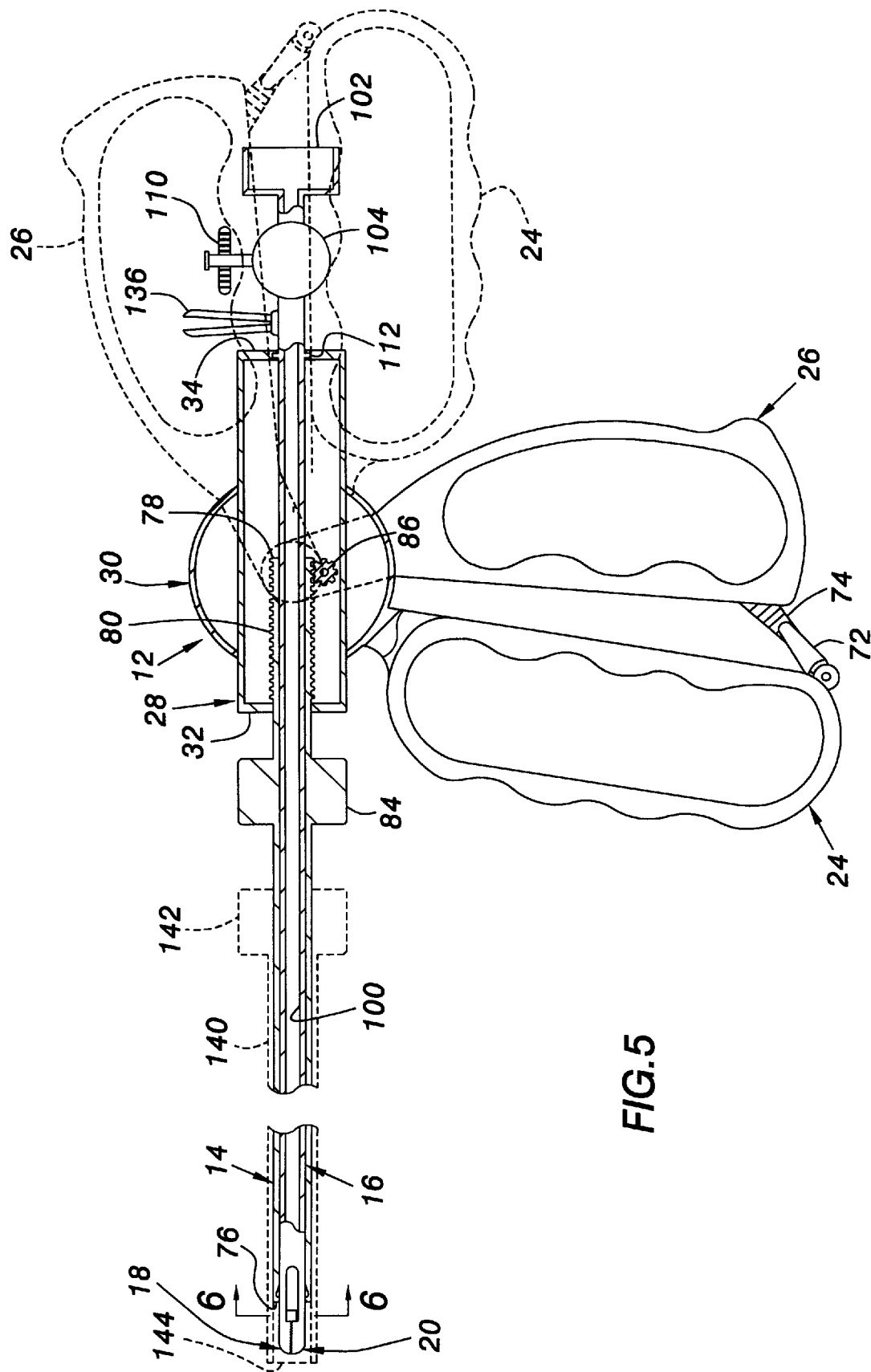
FIG. 5 is a broken side view, partly in section, of the multifunctional instrument of FIG. 1 with the jaws of the instrument in a closed position.
Figure 20:
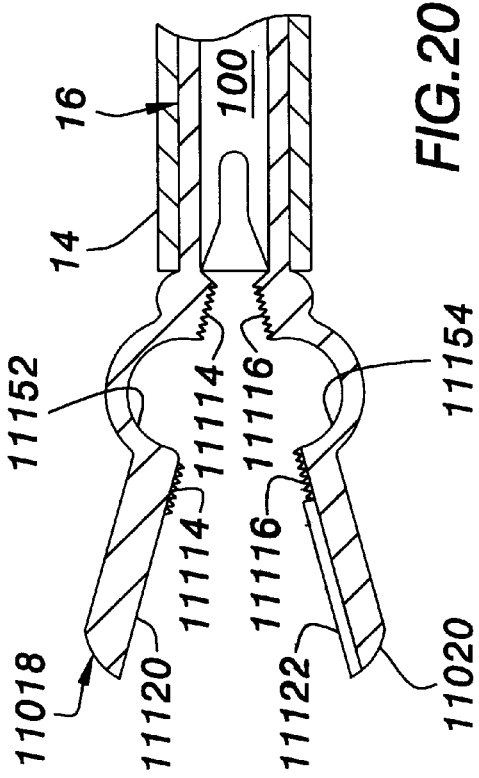

A third tubular member or sleeve, shown by broken lines in FIGS. 2 and 5 at 140, can optionally be disposed telescopically around the outer tubular member and provided with a collar 142 at a proximal end to permit manual movement of the sleeve in an axial direction relative to the outer tubular member between a retracted position where a distal end 144 of the sleeve is proximally spaced from or disposed adjacent the distal end of the outer tubular member to expose the jaws as shown in FIG. 2 and an extended position where the distal end of the third member is disposed distally of the distal end of the outer tubular member to cover the jaws as shown in FIG. 5.

In use, instrument 10 is grasped using finger loops 56 and 60 and is guided to the operative site directly via an incision in the wall of an anatomical cavity in the case of open surgery or via a portal sleeve positioned in the wall of an anatomical cavity in the case of endoscopic surgery. The portal sleeve can be positioned in the anatomical cavity wall using any suitable penetrating technique, including those creating puncture sites by means of removable obturators such as trocars, and can include a valve housing, if desired, to prevent loss of pneumoperitoneum during insertion and withdrawal of the instrument. Visualization of the endoscopic procedure can be accomplished using a conventional endoscope incorporated into the instrument, for example within the operating channel 100 defined by tubular shaft 98, or separately positioned within the anatomical cavity through a second portal sleeve located at another puncture site.

Instrument 10 is preferably advanced distally through the portal sleeve with jaws 18 and 20 in the closed position shown in FIG. 5 to minimize the size of the portal sleeve needed to communicate with the anatomical cavity and to prevent the jaws from catching on structure within the valve housing or portal sleeve. If desired, an outer sleeve such as the one shown by broken lines in FIG. 5 at 140 can be moved distally relative to the outer tubular member to cover the jaws prior to insertion for additional safety. Once the jaws have emerged into the anatomical cavity, the instrument can be manipulated externally of the body to position the jaws at the operative site. Various grasping and cutting functions can be performed at the operative site using different portions of the jaws and by operating the handles of the instrument to open and close the jaws as required. Since inner member 16 is fixed relative to housing 12, actuation of the jaws to open or close is controlled by moving outer tubular member 14 longitudinally relative to the inner member. If closed, jaws 18 and 20 can be opened by moving outer tubular member 14 proximally relative to inner member 16. If open, jaws 18 and 20 can be closed by moving outer tubular member 14 distally relative to inner member 16.

Movement of the outer tubular member over the inner member is controlled by the position of button 70 and operation of movable handle 26. More specifically, when button 70 is in an elevated or undepressed position or condition as shown by solid lines in FIG. 3, face gear 68 at the end of shaft 66 is outwardly spaced from face gear 94 such that rotation of the button shaft caused by movement of handle 26 will not result in movement of the outer tubular member. However, when button 70 is in a sunken or depressed position or condition as shown by broken lines in FIG. 3, face gear 68 at the end of shaft 66 meshingly engages face gear 94 such that rotation of the button shaft caused by movement of handle 26 is imparted to the outer tubular member via face gear 94 and gears 90, 86 and 88. For example, looking at FIGS. 2 and 3, it can be seen that counterclockwise rotation of handle 26 (in the sense of FIG. 2) will result in counterclockwise rotation of shaft 66 and face gear 68 at the inboard end of the shaft. Face gear 68 is meshed with face gear 94, movement of which also carries transmission gear 90 in a counterclockwise direction. Transmission gear 90 drives reduction gear 88 in a clockwise direction which, in turn, causes the shaft upon which pinion 86 is mounted to rotate in the clockwise direction opposite the rotation of the handle. Pinion 86 engages the gear teeth of rack 80 to cause proximal movement of the outer tubular member 14 relative to jaws 18 and 20 thereby permitting the jaws to move resiliently apart to the open position shown in FIG. 2. In the open position, jaws 18 and 20 are biased apart such that inner surfaces 114 and 116 of the jaws and cutting edges 124 and 126 of the blades are angularly spaced from one another allowing objects to be positioned in the space between different portions of the jaws to be grasped and/or cut. Conversely, clockwise rotation of the handle 26 about shaft 66 results in counterclockwise rotation of reduction gear 88 and pinion 86 causing distal movement of rack 80 and outer tubular member 14 relative to the jaws so that distal end 76 of the outer tubular member will slide over the jaws in an axial or longitudinal direction causing the jaws to be cammed laterally inward from the open position to the closed position. As the jaws move from the open position to the closed position, inner surfaces 114 and 116 will rotate toward another to grasp objects, such as needles or tissue, disposed therebetween, and cutting edges 124 and 126 of the blades will slidingly engage one another like a scissors to cut objects, such as tissue or lengths of suture material, placed between the blades when the jaws are in the open position.

Movable handle 26 is preferably proximally spaced from fixed handle 24 as shown so that the user can maintain one or more fingers on the stationary handle 24 while operating the movable handle 26 with the thumb and/or other fingers of the hand. In addition, movable handle 26 is preferably biased in a clockwise direction, looking at FIG. 3, toward stationary handle 24 so that, when the movable handle is released, outer tubular member 14 will be automatically moved over jaws 18 and 20 to cause the jaws to move laterally inward toward the closed position, for example to hold a suture needle between the jaws during complicated maneuvers requiring free hand movement.

In addition to performing various grasping and cutting functions, the surgical instrument 10 according to the present invention permits access to the operative site from outside the body through channel 100 formed along the inner member between proximal and distal ends of the instrument. The channel can, for example, be used to introduce lengths of suture material (with or without knotting elements attached thereto) as well as any other medical devices or instruments, such as endoscopes or probes, or to perform irrigation or aspiration at the operative site, for example by attaching a source of fluid or suction to the coupling at the proximal end of the inner member, or to administer medicaments as desired.

It will also be appreciated that when button 70 is in the elevated, undepressed position shown by solid lines in FIG. 3, end cap 36 may be rotated about an axis transverse to the longitudinal axis of the longitudinal housing portion to move the handles 24 and 26 between the transverse position shown by solid lines in FIG. 2 and the rearward facing position shown by broken lines in FIG. 2. Button 70 may then be depressed to maintain the handles in the desired angular orientation. The handles can also be rotated about the longitudinal axis of the inner and outer members by keying the inner member to rotate with the outer member (e.g., by forming a longitudinal groove in one member and carrying a mating rib or protrusion on the other member) and grasping collar 84 while turning housing 12. If, on the other hand, it is desired to rotate the jaws of the instrument without moving the handle, this can be accomplished by keying the inner member to rotate with the outer member and grasping the handle to maintain the housing in a stationary position while turning the collar in the desired direction. The relative angular orientation of the jaws and the handle can be maintained by frictional engagement of coupled components, the use of buttons or pins or any other suitable method of manually releasable fixation.

Figure 7:
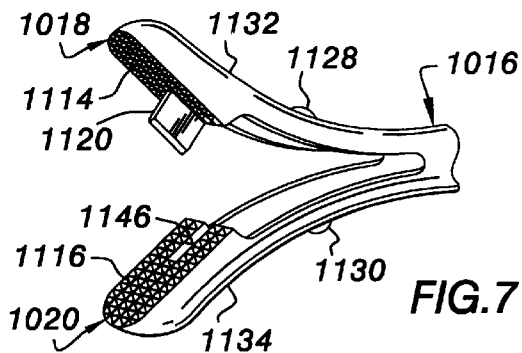
FIG. 7 is a fragmentary perspective view of the distal end of a modification of the multifunctional instrument according to the present invention with the jaws of the instrument in an open position.
Figure 8:
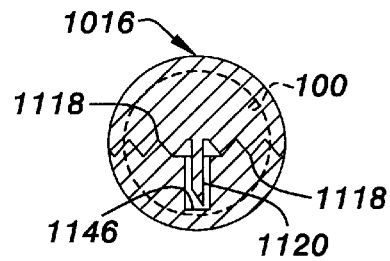
FIG. 8 is a cross-sectional view of the jaws of the multifunctional instrument of FIG. 7 in a closed position.

FIGS. 7 and 8 illustrate a modification of the jaws of the surgical instrument according to the present invention wherein the modified upper jaw 1018 carries a blade 1120 with a cutting edge 1124 and the modified lower jaw 1020 defines a concave recess or pocket 1146 for receiving the blade. Blade 1120 extends perpendicularly from a proximal end of inner surface 1114 of the needle holding or grasping portion of the upper jaw and is centrally located along the longitudinal axis of the inner member in opposed relation to the pocket, which is formed in the proximal end of inner surface 1116 of the needle holding or grasping portion of the lower jaw. Cutting edge 1124 of the blade is angularly spaced from the lower jaw when the jaws are in the open position as shown in FIG. 7, permitting anatomical tissue and other objects to be positioned between the blade and the pocket. When jaws 1018 and 1020 are closed, blade 1120 moves toward pocket 1146 and is received therein to cut any object held between the cutting portion of the jaws. As seen in FIG. 8, jaws 1018 and 1020 can be closed completely when blade 1120 is disposed within pocket 1146 and can thus be used to compress or flatten the tissue or object held therebetween if desired.

Figure 9:
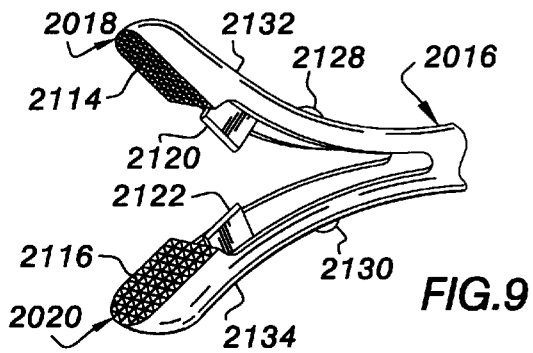
FIG. 9 is a fragmentary perspective view of the distal end of another modification of the multifunctional instrument according to the present invention with the jaws of the instrument in an open position.
Figure 10:
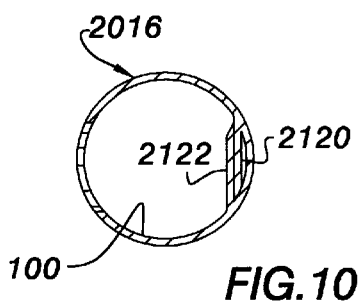
FIG. 10 is a cross-sectional view of the jaws of the multifunctional instrument of FIG. 9 in a closed position.

The modified jaws 2018 and 2020 shown in FIGS. 9 and 10 are similar to the jaws described above but carry a pair of blades 2120 and 2122 disposed proximally of inner grasping surfaces 2114 and 2116 in opposed relation along lateral edges of the jaws. Blades 2120 and 2122 depend perpendicularly from opposed lateral edges of the jaws and have opposed cutting edges 2124 and 2126 spaced apart when jaws 2018 and 2020 are open to permit positioning of anatomical tissue and other objects between the blades. When jaws 2018 and 2020 are closed, cutting edges 2124 and 2126 of the blades move towards one another and into sliding contact to cut any tissue or objects held between the jaws. As best seen in FIG. 10, the off-axis or eccentric position of the blades relative to the longitudinal axis of the inner member also facilitates visualization of the procedure through an endoscopic instrument positioned within operating channel 2100.

Figure 11:
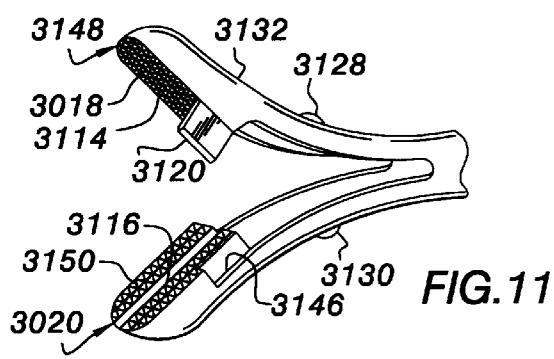
FIG. 11 is a fragmentary perspective view of the distal end of yet another modification of the multifunctional instrument according to the present invention with the jaws of the instrument in an open position.
Figure 12:
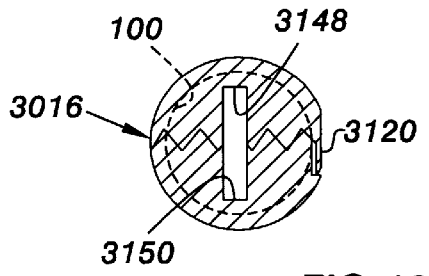
FIG. 12 is a cross-sectional view of the jaws of the multifunctional instrument of FIG. 11 in a closed position.

FIGS. 11 and 12 illustrate a further modification of the surgical instrument according to the present invention wherein the upper jaw 3018 carries a laterally offset, off-axis or eccentric blade 3120 with a cutting edge 3124 and the lower jaw 3020 defines a concave pocket 3146 for receiving the blade. Blade 3120 extends perpendicularly from a proximal end of inner surface 3114 of the needle holding or grasping portion of the upper jaw and is laterally spaced from the central longitudinal axis of the inner member to be disposed along an outer peripheral edge of the jaw in opposed relation to pocket 3146. Cutting edge 3124 of the blade is angularly spaced from pocket 3146 in lower jaw 3020 when the jaws are open permitting anatomical tissue and other objects to be positioned between the blade and the pocket. When jaws 3018 and 3020 are closed, blade 3120 moves toward pocket 3146 and is received therein to cut any tissue or object held between the jaws. Jaws 3018 and 3020 are also shown with longitudinal grooves or slots 3148 and 3150 which extend along the entire length of grasping surfaces 3114 and 3116 in opposed relation to define a passage or channel through the jaws when the jaws are closed. Such grooves can be formed in any of the jaws described herein and can be disposed along the central longitudinal axes of the jaws or offset therefrom dependent upon blade location. Furthermore, multiple grooves can be formed in laterally spaced relation in any of the jaws to define more than one channel if desired.

The grasping portion of the instrument jaws can be suitably configured to grasp any type of object during an endoscopic procedure. As described above, the grasping portion can be configured to include opposed surfaces which are caused to meet or come very close to one another to clamp objects such as needles positioned between the jaws by exerting a compressive force on the objects as the jaws are moved toward one another. Under certain circumstances, however, medical personnel may wish to hold an object without deforming or compressing the object, for example when moving or manipulating certain tubular organs. FIGS. 13–20 illustrate modifications of the endoscopic instrument wherein the jaws are provided with concave holding portions between which objects may be held without being deformed or compressed. In FIG. 13, the modified upper and lower jaws 4018 and 4020 include grasping surfaces 4114 and 4116 disposed distally of cutting members 4120 and 4122, respectively, and concave portions 4152 and 4154 of arcuate configuration which bend outwardly from the longitudinal axis of each jaw between the grasping surfaces and the cutting members in opposed relation to define a circular or other suitably shaped opening therebetween when the jaws are closed, the opening having a size and shape to surround selected objects, such as tubular vessels and organs, without substantially traumatically compressing the objects.

Figure 19:
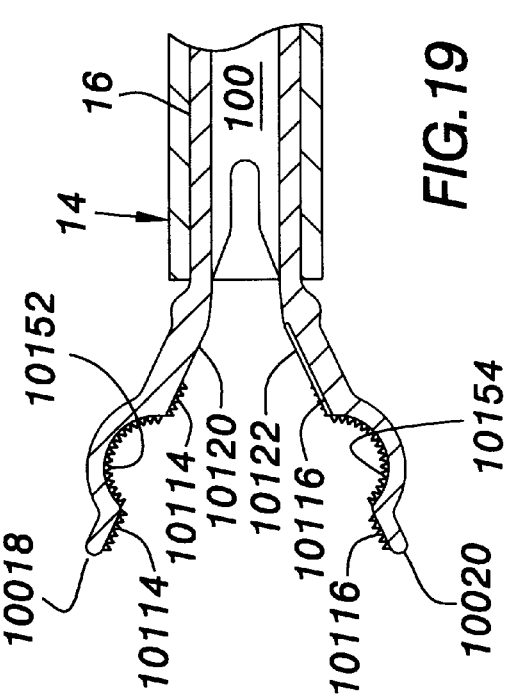

The modified instrument jaws 5018 and 5020 shown in FIG. 14 are similar to those shown in FIG. 13 but with concave portions 5152 and 5154 disposed proximally of grasping surfaces 5114 and 5116, and cutting members 5120 and 5122 disposed between the concave portions and the grasping surfaces. Another modification of the instrument jaws is shown in FIG. 15 wherein upper and lower jaws 6018 and 6020 are similar to those described above but with concave portions 6152 and 6154 disposed distally of cutting members 6120 and 6122, and grasping surfaces 6114 and 6116 disposed between the concave portions and the cutting members. In the modification of the instrument jaws shown in FIG. 16, upper and lower jaws 7018 and 7020 are similar to those described above but with grasping surfaces 7114 and 7116 disposed proximally of cutting members 7120 and 7122, and concave portions 7152 and 7154 disposed between the grasping surfaces and the cutting members. The modified instrument jaws 8018 and 8020 shown in FIG. 17 are similar to those described above but with concave portions 8152 and 8154 disposed distally of grasping surfaces 8114 and 8116, and cutting members 8120 and 8122 disposed between the concave portions and the grasping surfaces. Yet another modification of the instrument jaws is shown in FIG. 18 wherein upper and lower jaws 9018 and 9020 are similar to those described above but with concave portions 9152 and 9154 disposed proximally of cutting members 9120 and 9122, and grasping surfaces 9114 and 9116 disposed between the concave portions and the cutting members. In FIG. 19, another modification of the instrument jaws is shown wherein upper and lower jaws 10018 and 10020 are similar to those described above in connection with FIG. 13 but with grasping surfaces 10114 and 10116 disposed proximally and distally of concave portions 10152 and 10154, and cutting members 10120 and 10122 disposed proximally of the grasping surfaces. Similarly, in FIG. 20, still another modification of the instrument jaws is shown wherein upper and lower jaws 11018 and 11020 are similar to those shown in FIG. 16 but with grasping surfaces 11114 and 11116 disposed proximally and distally of concave portions 11152 and 11154, and cutting members 11120 and 11122 disposed distally of the grasping surfaces.

From the above, it will be appreciated that the instrument according to the present invention permits multiple grasping and cutting functions to be performed in endoscopic and open surgery with a single instrument while defining a channel for fluids and other medical instruments and probes to be communicated at the operative site without the need of having to remove the instrument from the body.

Figure 21:
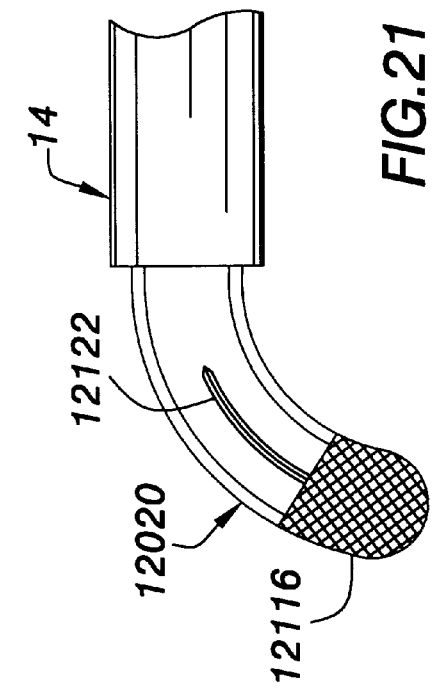
FIG. 21 is a top view of a lower jaw of the multifunctional instrument showing yet another modification of the instrument jaws according to the present invention.

The jaws making up the jaw portion of the instrument can be formed as an integral one-piece unit or assembled from separate pieces; and, depending on procedural use, one of the jaws can be fixed and the other movable, both jaws can be movable, the jaws can be linked by pivots or formed at the end of a tubular member or formed at the end of a pair of pivotally connected arms. The jaws, including any of the grasping or cutting portions thereof, can be straight, curved and/or angled as desired. For example, in FIG. 21, a jaw 12020 and blade 12120 are shown bending outwardly from the longitudinal axis of the outer tubular member in a curved configuration. Any of the jaws shown or described herein can be formed with opposed inner surfaces formed of repeated patterns of diamond-shaped protrusions, lateral and/or longitudinal ribs and/or other types of structural features suitable for holding needles and other types of objects during an endoscopic procedure. The jaws can have any shape in transverse cross-section when closed including, but not limited to, circular, elliptical, rectangular and polygonal configurations, and can have opposed arcuate or concave portions for holding objects, such as tubular organs, without traumatically compressing the objects. The jaws can also be of varying width in the longitudinal direction such that, for example, relatively thin cutting members or blades can be formed along a first longitudinal portion of the jaws and grasping portions of greater width than the cutting members can be formed at longitudinally spaced locations relative to the cutting members.

The cutting members or blades can be carried by one or both jaws and centrally located for cutting anatomical tissue, unsecured lengths of suture material or any other objects normally cut during a surgical procedure, or the blades can be offset laterally from the central longitudinal axis of the jaws to permit better visualization and to allow the formation of longitudinal grooves or openings through the jaws when closed. If a single blade is carried by one jaw, the other jaw can carry an opposed blade in a manner to permit sliding contact with scissor-like cutting, direct abutment of cutting edges to produce a chopping cut, and/or can form a pocket for receiving the cutting edge of the opposed blade to permit partial or complete closure of the jaws together. Furthermore, the blades can have straight, curved or angled cutting edges and can be oriented at any angle relative to a longitudinal axis of the jaws.

The handle portion of the endoscopic instrument shown and described herein is exemplary of the types of conventional handle mechanisms suitable for performing the function of actuating the jaws; accordingly, the handles can have any configuration to actuate the jaws including, but not limited to, configurations employing a pair of pivotally connected arms, one fixed and one pivoted arm, a pistol grip with a movable trigger, or resilient U-shaped handle members. Further, the handle portion of the instrument can be configured in any suitable manner to rotate relative to a pivot axis oriented perpendicular to the longitudinal axis of the instrument so that, for example, in one position the handles will extend laterally from the instrument or at a substantially perpendicular angle relative to the longitudinal axis; while, in another position, the handles will extend proximally from the instrument like scissor handles.

It will be appreciated that the handle portion and jaw portion of the endoscopic instrument can be integrally formed as a one-piece unit or formed as separate components and coupled together, for example, by use of pivots, linkages, rods, cables, telescoping members, brackets and other mechanical and/or electrical couplings.

When the instrument is formed of telescoping members, it will also be appreciated that individual tubular members, such as the inner member can be made rotatable about a longitudinal axis of the instrument either alone or in combination with other telescoping members. Moreover, when the instrument is coupled with a source of fluid or suction, an operating unit or other medical device, the instrument housing can have any configuration for being releasably coupled including, but not limited to threaded or telescoping portions, detents, latches or any other suitable connections. Furthermore, the housing can be cylindrical or rectangular or have any other useful or convenient configuration in cross-section.

The inner member can define one channel as shown or multiple channels of similar or different cross-sectional configuration. Any of the channels defined by the inner member can be coaxially disposed or offset from the central longitudinal axis of the inner member and can have any suitable configuration in cross-section dependent upon procedural use including, but not limited to, circular, elliptical and polygonal cross-sectional configurations.

Figure 22:
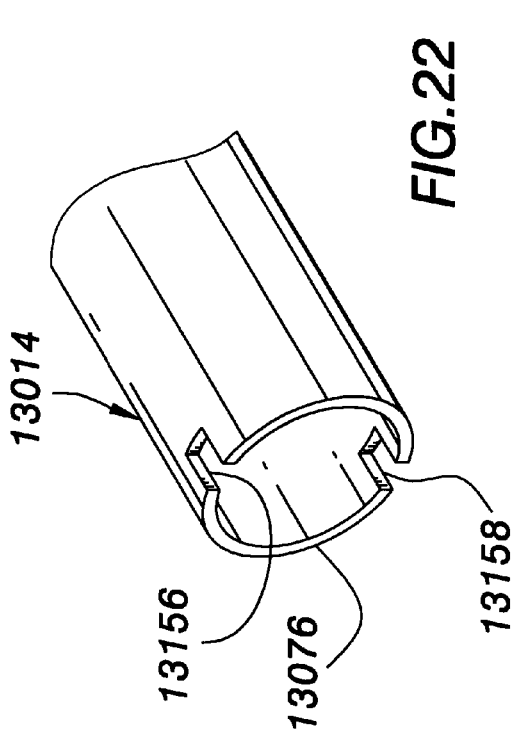
FIG. 22 is a fragmentary perspective view of a modification of the outer tubular member of the multifunctional instrument according to the present invention.

The outer tubular member can have any suitable configuration in cross-section to fit through a portal formed in the wall of an anatomical cavity and to receive the inner member for sliding movement therein. The distal end of the outer tubular member can be blunt, tapered, beveled or chamfered, and can also be provided with longitudinal slots (for example, as shown in FIG. 22 where slots 13156 and 13158 extend proximally from diametrically opposed positions at the distal end of the outer tubular member 13014) or interior grooves for receiving protrusions or cams carried on the outer surfaces of the jaws to assist in maintaining proper alignment of the jaw blades when cutting tough materials. Alternatively, protrusions can be carried on an interior surface of the outer tubular member in alignment with slots or grooves formed in the jaws to maintain alignment during operational use.

The components of the endoscopic instrument of the present invention can be made of any suitable, medical grade materials to permit sterilization for reuse or disposal for single patient use. The components can be made of multiple parts of various configurations and materials to reduce cost and/or simplify fabrication. The instrument can have various valves, stop cocks and seals in the housing and/or inner member to control fluid flow therethrough.

The features of the various embodiments described above can be combined in any manner desired dependent upon the operational requirements of the procedure to be performed and the complexity of the endoscopic instrument.

Inasmuch as the present invention is subject to many variations, modifications and changes to detail it is intended that all subject matter discussed above or shown in the accompanying drawings be interpreted as illustrative only and not be taken in a limiting sense.

What is claimed is:

1. A multifunctional instrument for use in performing endoscopic and open surgical procedures within an anatomical cavity comprising
   a handle;
   an elongate member having a proximal end coupled with said handle for being disposed externally of the anatomical cavity and a distal end for being disposed within the anatomical cavity;
   a pair of opposed, relatively movable jaws carried at said distal end of said elongate member;
   said jaws defining a grasping portion operable by manipulation of said handle to grasp objects in the anatomical cavity;
   said jaws defining a cutting portion operable by manipulation of said handle to cut objects in the anatomical cavity;
   an operating channel defined along said elongate member and having an open proximal end adjacent said proximal end of said elongate member and an open distal end adjacent said distal end of said elongate member to define a passage communicating between an exterior of the anatomical cavity and an operative site in the anatomical cavity when said distal end of said elongate member is positioned within the anatomical cavity; and a valve disposed along said operating channel to control access to the operative site through said operating channel.

2. A multifunctional instrument for use in performing endoscopic and open surgical procedures within an anatomical cavity as recited in claim 1 wherein said cutting portion includes a blade.

3. A multifunctional instrument for use in performing endoscopic and open surgical procedures within an anatomical cavity as recited in claim 1 wherein said cutting portion includes a pair of blades carried by said jaws in opposed relation.

4. A multifunctional instrument for use in performing endoscopic and open surgical procedures within an anatomical cavity as recited in claim 1 wherein said cutting portion includes a blade carried by a first of said jaws and a recess formed in a second of said jaws in opposed relation to said blade to receive said blade when said jaws are moved toward one another.

5. A multifunctional instrument for use in performing endoscopic and open surgical procedures within an anatomical cavity as recited in claim 2 wherein said blade is oriented parallel to a longitudinal axis of said elongate member.

6. A multifunctional instrument for use in performing endoscopic and open surgical procedures within an anatomical cavity as recited in claim 5 wherein said blade is disposed along a central longitudinal axis of said elongate member.

7. A multifunctional instrument for use in performing endoscopic and open surgical procedures within an anatomical cavity as recited in claim 5 wherein said blade is laterally offset from a central longitudinal axis of said elongate member.

8. A multifunctional instrument for use in performing endoscopic and open surgical procedures within an anatomical cavity as recited in claim 2 wherein said blade is curved relative to a longitudinal axis of said elongate member.

9. A multifunctional instrument for use in performing endoscopic and open surgical procedures within an anatomical cavity as recited in claim 2 wherein said jaws bend outwardly in a lateral direction relative to a longitudinal axis of said elongate member when closed together.

10. A multifunctional instrument for use in performing endoscopic and open surgical procedures within an anatomical cavity as recited in claim 9 wherein said jaws are of curved configuration when closed together.

11. A multifunctional instrument for use in performing endoscopic and open surgical procedures within an anatomical cavity as recited in claim 1 wherein said grasping portion is longitudinally spaced from said cutting portion to hold a needle.

12. A multifunctional instrument for use in performing endoscopic and open surgical procedures within an anatomical cavity as recited in claim 1 wherein said jaws include opposed concave portions longitudinally spaced from said cutting portion for defining an opening between the jaws to hold an object during a surgical procedure without compressing the object.

13. A multifunctional instrument for use in performing endoscopic and open surgical procedures within an anatomical cavity as recited in claim 1 wherein said grasping portion is disposed distally of said cutting portion and wherein at least one of said jaws includes a concave portion between said grasping portion and said cutting portion to hold an object during a surgical procedure without compressing the object.

14. A multifunctional instrument for use in performing endoscopic and open surgical procedures within an anatomical cavity as recited in claim 1 wherein at least one of said jaws includes a concave portion distally spaced from said cutting portion to hold an object during a surgical procedure without compressing the object and wherein said grasping portion is disposed between said concave portion and said cutting portion.

15. A multifunctional instrument for use in performing endoscopic and open surgical procedures within an anatomical cavity as recited in claim 1 wherein said grasping portion is disposed distally of said cutting portion and at least one of said jaws includes a concave portion proximally spaced from said cutting portion to hold an object during a surgical procedure without compressing the object.

16. A multifunctional instrument for use in performing endoscopic and open surgical procedures within an anatomical cavity as recited in claim 1 wherein said grasping portion is proximally spaced from said cutting portion and at least one of said jaws includes a concave portion distally spaced from said cutting portion to hold an object during a surgical procedure without compressing the object.

17. A multifunctional instrument for use in performing endoscopic and open surgical procedures within an anatomical cavity as recited in claim 1 wherein said grasping portion is proximally spaced from said cutting portion and at least one of said jaws includes a concave portion disposed between said grasping portion and said cutting portion to hold an object during a surgical procedure without compressing the object.

18. A multifunctional instrument for use in performing endoscopic and open surgical procedures within an anatomical cavity as recited in claim 1 wherein at least one of said jaws includes a concave portion proximally spaced from said cutting portion to hold an object during a surgical procedure without compressing the object and wherein said grasping portion is disposed between said concave portion and said cutting portion.

19. A multifunctional instrument for use in performing endoscopic and open surgical procedures within an anatomical cavity as recited in claim 1 wherein at least one of said jaws includes a concave portion distally spaced from said cutting portion to hold an object during a surgical procedure without compressing the object and wherein said grasping portion includes a first portion disposed distally of said concave portion and a second portion disposed between said concave portion and said cutting portion.

20. A multifunctional instrument for use in performing endoscopic and open surgical procedures within an anatomical cavity as recited in claim 1 wherein said elongate member is of tubular configuration with proximal and distal ends of said elongate member being open and wherein said valve is disposed between said proximal and distal ends.

21. A multifunctional instrument for use in performing endoscopic and open surgical procedures within an anatomical cavity as recited in claim 1 and further comprising a coupling disposed at said proximal end of said operating channel for connection with other medical instruments.

22. A multifunctional instrument for use in performing endoscopic and open surgical procedures within an anatomical cavity as recited in claim 1 wherein said jaws are biased apart in a lateral direction relative to a longitudinal axis of said elongate member toward an open position and further comprising an outer tubular member disposed telescopically around said elongate member and having a proximal end coupled with said handle and a distal end axially movable relative to said elongate member by manipulation of said handle between a retracted position allowing said jaws to move apart toward said open position and an extended position causing said jaws to move together toward a closed position.

23. A multifunctional instrument for use in performing endoscopic and open surgical procedures within an anatomical cavity as recited in claim 22 wherein at least one of said jaws includes a cam extending outwardly therefrom in a lateral direction relative to said longitudinal axis of said elongate member and said outer tubular member includes a distal end having a peripheral edge with a slot extending proximally therefrom in alignment with said cam to receive said cam when said outer tubular member is in said extended position.

24. A multifunctional instrument for use in performing endoscopic and open surgical procedures within an anatomical cavity as recited in claim 22 wherein each of said jaws includes a cam extending outwardly therefrom in a lateral direction relative to said longitudinal axis of said elongate member and said outer tubular member includes a distal end having a peripheral edge with slots extending proximally therefrom in alignment with said cams to receive said cams when said outer tubular member is in said extended position.

25. A method of performing a surgical procedure in an anatomical cavity comprising the steps of introducing an elongate member with opposed, relatively movable jaws at a distal end through an opening in a wall of the anatomical cavity;

utilizing a first portion of the jaws to cut an object at an operative site in the anatomical cavity; and accessing the operative site from outside the body using an operating channel defined along the elongate member.

26. A method of performing a surgical procedure in an anatomical cavity as recited in claim 25 and further comprising the step of utilizing a second portion of the jaws to grasp an object at the operative site.

27. A method of performing a surgical procedure in an anatomical cavity as recited in claim 25 and further comprising the step of utilizing opposed concave portions of the jaws to hold an object without compressing the object.

28. A method of performing a surgical procedure in an anatomical cavity as recited in claim 25 and further comprising the step of controlling access to the operative site through the operating channel by manually operating a valve disposed along the operating channel.

* * * * *